United States Patent [19]

Schon et al.

[11] Patent Number: 5,718,692
[45] Date of Patent: Feb. 17, 1998

[54] SELF-RETAINING SINGLE INSERTION DOUBLE CATHETER ASSEMBLY AND METHOD FOR MAKING DOUBLE CATHETER SYSTEMS

[75] Inventors: Donald Schon, Phoenix, Ariz.; Anthony J. Madison, Harleysville, Pa.

[73] Assignees: Twineath, L.L.C., Phoenix, Ark.; Medical Component, Inc., Harleysville, Pa.

[21] Appl. No.: 471,263

[22] Filed: Jun. 6, 1995

[51] Int. Cl.⁶ .................................... A61M 25/00
[52] U.S. Cl. ...................... 604/264; 604/43; 604/280
[58] Field of Search ...................... 604/19, 27, 29, 604/39, 43, 48–9, 52–3, 93–4, 117, 173–5, 179–180, 264, 280, 283.4, 905; 128/656–8; 606/108, 199

[56] References Cited

U.S. PATENT DOCUMENTS

| | | | |
|---|---|---|---|
| 3,400,714 | 9/1968 | Sheridan . | |
| 4,098,275 | 7/1978 | Consalvo . | |
| 4,385,631 | 5/1983 | Uthmann | 604/43 |
| 4,402,683 | 9/1983 | Kopman | 604/175 |
| 4,405,313 | 9/1983 | Sisley et al. | 604/53 |
| 4,427,012 | 1/1984 | Miller | 128/654 |
| 4,451,252 | 5/1984 | Martin | 604/43 |
| 4,493,696 | 1/1985 | Uldall | 604/43 |
| 4,548,597 | 10/1985 | Nelson | 604/43 |
| 4,619,643 | 10/1986 | Bai | 604/43 |
| 4,687,471 | 8/1987 | Twardowski et al. | 604/29 |
| 4,898,669 | 2/1990 | Tesio . | |
| 5,057,075 | 10/1991 | Moncrief et al. | 604/175 |
| 5,084,013 | 1/1992 | Takase | 604/43 |
| 5,156,592 | 10/1992 | Martin et al. | 604/43 |
| 5,167,220 | 12/1992 | Brown | 604/280 |
| 5,209,723 | 5/1993 | Twardowski et al. | 604/43 |
| 5,334,167 | 8/1994 | Cocanower | 604/280 |
| 5,336,220 | 8/1994 | Ryan et al. | 604/22 |
| 5,364,377 | 11/1994 | O'Neil | 604/905 |
| 5,385,548 | 1/1995 | Williams et al. | 604/96 |
| 5,480,380 | 1/1996 | Martin | 604/43 |

OTHER PUBLICATIONS

B. Canaud, J.J. Beraud, H. Joyeux, C. Miou, "Internal Jugular Vein Cannulation with Two Silicone Rubber Catheters: A New and Safe Temporary Vascular Access for Hemodialysis", Artificial Organs 1986; 10(5): 397–403.

F. Tesio et al., "Double Catheterization of the Internal Jugular Vein for Hemodialysis: Indications, Techniques, and Clinical Results", Artificial Organs 1994; 18(4): 301–304.

*Primary Examiner*—Michael Buiz
*Assistant Examiner*—Jennifer R. Sadula
*Attorney, Agent, or Firm*—Panitch Schwarze Jacobs & Nadel, P.C.

[57] ABSTRACT

A self-retaining catheter assembly is provided which includes a first and second catheter and a retaining sleeve. The first and second catheters each have an exterior surface and an interior surface defining a lumen which extends longitudinally through the catheter. The first catheter has a proximal portion which is for placement within a first subcutaneous area, and the second catheter has a proximal portion which is for placement within a second subcutaneous area. The first and second catheters also each have distal portions for placement within an area to be catheterized. The retaining sleeve is positioned around a portion of the exterior surfaces of the catheters which is located proximal to the distal portions of the catheters. The portions of the exterior surfaces of the catheters within the retaining sleeve are in a juxtaposed relationship and the retaining sleeve is positioned such that when the distal portions of the first and second catheters are within the area to be catheterized, the retaining sleeve is outside the area to be catheterized and distal to the first and second subcutaneous areas, and the assembly is secured in place.

19 Claims, 2 Drawing Sheets

FIG. 5

SELF-RETAINING SINGLE INSERTION DOUBLE CATHETER ASSEMBLY AND METHOD FOR MAKING DOUBLE CATHETER SYSTEMS

FIELD OF THE INVENTION

The present invention relates to self-retaining double catheter assemblies which may be positioned within the body using only a single insertion and a method for making double catheter systems self-retaining.

BACKGROUND OF THE INVENTION

Catheters may be located in various venous locations and cavities throughout the body. Central venous catheters, for example, are placed in four common locations within the chest and/or in the femoral vessels. They may be placed, for example, in either the right or left subclavian vein or in the right or left internal jugular vein.

In order to place a catheter in a particular location, a physician uses various techniques. To determine the location of some vessels, for example, a physician may predict the location by physical body landmarks present on the body surface for vessels which are not themselves visible on the body surface. Using landmarks, vessels may be cannulated by first identifying the vessels by aspiration with a long hollow needle. When blood enters a syringe attached to the needle, the syringe is disconnected and a thin guide wire is passed through the needle into the hollow passage, or lumen, of the vessel. The needle is then removed leaving the guide wire within the vessel. The guide wire projects beyond the surface of the skin.

At this point, several options are available to a physician for catheter placement. The simplest is to pass a catheter into the vessel directly over a guide wire. The guide wire is then removed leaving the catheter in position within the vessel. However, this technique is only possible in cases where the catheter is of a relatively small diameter, made of a stiff material and not significantly larger than the guide wire, for example, for insertion of small diameter dual lumen catheters. If the catheter to be inserted is significantly larger than the guide wire, a dilator device is first passed over the guide wire to enlarge the hole following which the catheter is passed over the guide wire and the guide wire and dilator removed.

In the case of an individual, single-lumen catheter, such as a Tesio catheter, a physician may use a further option including use of an introducer sheath. A Tesio catheter is generally used as a part of a double catheter system in which two individual single-lumen catheters are inserted in two different locations for removing and introducing fluids to an area of the body to be catheterized. For example, the catheters may be used for hemodialysis by inserting each catheter in two separate femoral veins, or by inserting each catheter in two different locations of the same vein, such as the internal jugular vein. The introducer sheath is simply a large, stiff thin-walled tube which serves as a temporary conduit for the permanent catheter which is being placed. The introducer sheath is positioned by placing a dilator device inside of the introducer and passing both the dilator and the introducer together into the vessel. A guide wire left in the vessel after insertion by syringe as described above, and the dilator are then removed leaving the thin-walled introducer sheath in place. The catheter is then placed through this dilator sheath.

In the case of a Tesio catheter, a physician would not leave the stiff, thin-walled sheath in place. The catheter, without a hub or an anchoring device, may be passed through the sheath and into the vessel. The sheath is removed over the catheter. When a connecting means such as a hub, or any type of anchoring device such as a Dacron® or other fabric anchoring cuff is permanently attached to the catheter, the sheath must be large or comprise a tear-away portion which splits into two parts as the sheath is retracted. Once inserted, the catheter must be stabilized.

Typical anchoring devices for such catheters and other venous and body cavity catheters and shunts involve use of a tissue ingrowth cuff, generally made of a fabric such as Dacron® or the like, fitted on a proximal portion of the catheter for stabilization of the catheter in a single position if the catheter is to be left in that position for a significant length of time. Surrounding tissue cells grow into the fabric stabilizing the catheter in that particular location. In using catheters having a fabric cuff, or other retaining devices or fittings, one stabilizing technique includes creating a subcutaneous tunnel, or similar opening, several centimeters caudal to the insertion site of the catheter for stabilization of the catheter using the cuff or other device. Subcutaneous tunnels and stabilizing devices are typically used, for example, for insertion of Tesio catheters.

Once the catheter is inserted in a blood vessel or other location, the skin is anaesthetized in a linear fashion for a distance of about 6-8 centimeters caudal to the insertion site. If tunneling is used for venous insertion, a second incision is made and a tunneling device is passed into the incision and out through the skin at the point of catheter insertion creating a subcutaneous tunnel. The catheter is attached to the tunneling device and pulled back through the skin tunnel. A cuff is typically designed to lie in the medial portion of the subcutaneous tunnel. Similarly, when inserting catheters in body cavities and other locations, some catheters are designed such that the cuff is affixed to the catheter in an area which corresponds to a typical area chosen by a physician for subcutaneous securement.

Most fabric cuffs are not locatable or movable along the catheter to adjust for subcutaneous placement discrepancies. As most patients vary in size, internal distances involved in subcutaneous placement vary accordingly, deviating from the standard catheter cuff locations commercially available and making stable securement difficult in many cases. In addition, as these cuffs are typically non-movable, the physician may have to adjust the catheter itself within the vein to align the cuff within a stable area for securement. Positioning of the catheter is particularly important to proper catheter functioning. For example, if the tip of a central venous catheter is not properly located within a vessel, the catheter may cause the condition of cardiac arrhythmia or otherwise inhibit blood flow. If the catheter tip is not properly located within a body cavity there may not be sufficient access to the tip to allow bodily fluid to properly flow through the catheter.

The design limitations of single-insertion, multiple lumen catheters necessarily limit the size of the lumens and the location, number and size of the intake and return openings of the devices in order to easily insert these catheters over a guide wire without the use of a sheath or similar device and by using a single needle entry method for insertion. For example, in a double-lumen catheter having semi-circular lumens, while the device can be inserted using only one surgical opening directly over a guide wire, the size of the intake and return lumens each are limited by the small diameter of the device. Further, as such a device is unitary, additional apertures for intake and return flow of bodily fluid can only be provided over 180° provided by the semi-circular outer portion of each lumen. These smaller openings are necessary for catheter access if the primary distal luminal openings of the device become clogged or otherwise blocked, for example, if the tip is embedded in or suctioned to a vessel wall. Further, the typical longitudinal separation between the distal tip return opening and the proximally spaced intake opening of multiple lumen catheters of two centimeters does not always sufficiently prevent recirculation of intake and return fluids.

Use of a co-axial multiple lumen design allows for multiple openings in the outer intake lumen of the catheter which can be provided over the full 360° around the exterior of the catheter. This provides for a more stable catheter, particularly if used in a blood vessel for hemodialysis, because the draw of blood inward by the dialysis device is less likely in co-axial designs to pull the distal end of the catheter to one side thereby helping to minimize suction of the distal end against the vessel wall. This also helps to minimize harm to the vessel and the possibility of stenosis. Instead, the draw of blood is equal on all sides, helping to center the catheter in the vessel and providing for less overall vibration of the inserted portion of the catheter within the vessel due to the evenly distributed intake and co-axial return flow. In addition, the design reduces the chances of recirculation and suctioning to the vessel wall which may cause vessel trauma and/or blockage of the luminal openings. However, the design requirements of a co-axial lumen do not typically allow for additional openings in the inner, return lumen. The circular cross-sections of the lumens provide good fluid flow properties within the lumens. However, as with the semi-circular designs, the size of the lumens and the flow rate are typically dictated by the smaller size of the device which is the result of the need to easily insert the device over a guide wire in a single incision, or single-needle entry method.

A double catheter system using two, single-lumen catheters has several advantages and disadvantages when compared to the use of conventional multiple lumen catheters for infusion, perfusion, hemodialysis and the like. A Tesio system, using two, single-lumen catheters eliminates most of the disadvantages of multiple lumen catheters. Flow conditions are excellent due to the larger, circular cross-section of each of the individual lumens. There is less chance of catheter blockage, recirculation or vessel wall trauma, because the lumens are separately inserted in two different locations, and their distal end openings are not typically placed as close together as are the distal end openings of unitary multiple lumen catheters. The result is two independent lumens within the vessel. In addition, multiple additional apertures can be provided to both the intake and return catheters over the full 360° of each catheter in the system since the device is not unitary.

The disadvantages of existing Tesio systems are that they require a two separate needle insertion procedures, including two surgical incisions. As a consequence, the Tesio system also requires two subcutaneous tunnels, and two corresponding subcutaneous catheter anchoring devices such as fabric cuffs or related tunnel stabilizing devices. In comparison with a multiple lumen catheter and single-needle entry, the time for the surgical procedure is doubled. In addition, the use of two separate incisions into the body increases the possibility of infection, the possibility of bleeding and the potential for pneumothorax. If both of the catheters in the system are located in a single vessel for hemodialysis, the distal end openings of each catheter must be positioned correctly in the vessel, and must be accurately, longitudinally spaced from each other to avoid possible recirculation problems. The proximal portions of the catheters which lie within the tunnels must also be properly aligned such that the stabilizing devices within the tunnels are properly seated. All of these factors tend to complicate insertion and make use of such double catheter systems less desirable.

Based upon the foregoing, there is a general need in the art for a double catheter system in which each catheter can be stabilized independently of the location of individual anchoring devices within a subcutaneous tunnel or other subcutaneous location such that the individual catheters do not have to be adjusted after insertion and placement within a vessel or body cavity. In addition, it would be desirable to have a double catheter system which incorporates all the advantages of double catheter systems, but which eliminates such disadvantages as the need for double surgical incisions, the use of a double-needle entry, the need for anchoring each catheter in a separate subcutaneous location, the difficulty in exactly positioning the distal ends of the individual catheters relative to each other when inserted in the same vessel or cavity, the increased chance of infection corresponding to the longer procedure and multiple incisions into the body, the increased bleeding and the potential of pneumothorax.

There is also a need in the art for a double catheter system which incorporates the foregoing attributes, and which further functions with new dialysis equipment to speed dialysis treatment. Many new dialysis machines include high efficiency purification membranes which are more biocompatible and less likely to induce cardiovascular instability. Due to the increasing cost of health care, many hospitals are also attempting to reduce the time required for many procedures. Dialysis typically requires four hours of treatment time. Reducing the time a patient stays on a dialysis machine will save cost and benefit the patient being treated, as the patient would not have to be attached to the dialysis unit for such a significant length of time per treatment. Typically dialysis machines process fluid, in this case blood, at flow rates of about 250 cc/min. The new machines are capable of efficiently processing flow rates of about 450 cc/min, however, conventional multiple lumen catheters, due to the small lumen size, cannot adequately process very high flow rates without an increase in clotting.

In addition, in order to try to process higher flow rates with conventional multiple lumen catheters, the catheters are generally inserted deeper toward the atrium of the heart which can be dangerous in some situations. Use of traditional double catheter systems having two single-lumen catheters are difficult to place. Therefore, to move one of the lumens closer to the heart without careful placement of both lumens can be a very intricate procedure.

In view of the new machines and rising health care costs, there is a further need in the art for a system having the advantages previously mentioned which can safely process higher flow rates achievable with high efficiency dialysis machines, which does not have an increase in clotting under higher flow rates, and which is safer and more precisely placed close to the right atrium of the heart. In addition, there is a need for such a double catheter system which helps to minimize recirculation present in prior art catheter designs by safely increasing the longitudinal distance between the return and intake lumens, and separating the return and intake lumens at their respective distal openings.

SUMMARY OF THE INVENTION

The present invention includes a self-retaining double catheter assembly. The assembly includes a first catheter having an exterior surface, an interior surface defining a first lumen extending longitudinally through the first catheter, a proximal portion for placement within a first subcutaneous area, and a distal portion for placement within an area to be catheterized. The distal end of the distal portion of the first catheter has a first opening therethrough. The assembly also includes a second catheter having an exterior surface, an interior surface defining a second lumen extending longitudinally through the second catheter, a proximal portion for placement within a second subcutaneous area, and a distal portion for placement within the area to be catheterized. The distal end of the distal portion of the second catheter has a second opening therethrough. The assembly further includes a retaining sleeve positioned around a portion of the exterior surface of the first catheter located proximal to the distal portion of the first catheter and around a portion of the exterior surface of the second catheter located proximal to the distal portion of the second catheter. The portions of the exterior surfaces of the first and second catheters within the retaining sleeve are in a juxtaposed relationship. The retaining sleeve is positioned such that when the distal portions of the first and second catheters are within the area to be catheterized, the retaining sleeve is outside the area to be catheterized and distal to the first and second subcutaneous areas, and the assembly is secured in place.

The present invention also includes an improvement to a double catheter system comprising first and second catheters each having a first lumen extending longitudinally therethrough. A distal portion of the first catheter and a distal portion of the second catheter in the system are configured to be placed within an area to be catheterized. A proximal portion of the first catheter and a proximal portion of the second catheter are configured to be placed within a first and second subcutaneous area respectively. The improvement includes positioning a retaining sleeve around a portion of the first catheter and a portion of the second catheter such that the portions of the first and second catheters within the retaining sleeve are juxtaposed. The retaining sleeve is positioned such that when the distal portions of the first and second catheters are within the area to be catheterized, the retaining sleeve is located outside the area to be catheterized and distal to the first and second subcutaneous areas, and the first and second catheters are secured in place.

The present invention further includes a method for making a double catheter system self-retaining. The system includes a first catheter having an exterior surface, a distal portion for insertion into an area to be catheterized, a proximal portion for placement in a first subcutaneous area, and a first lumen extending longitudinally through the first catheter. The system also includes a second catheter having an exterior surface, a distal portion for insertion into the area to be catheterized, a proximal portion for placement in a second subcutaneous area, and a second lumen extending longitudinally through the second catheter. The method includes positioning a portion of the exterior surface of the first catheter and a portion of the exterior surface of the second catheter in a juxtaposed relationship within a retaining sleeve. Upon insertion of the distal portions of the first and second catheters into the area to be catheterized, the retaining sleeve is outside the area to be catheterized and distal to the first and second subcutaneous areas, and the first and second catheters are secured in place.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings, like numerals are used to indicate like elements throughout. In the drawings.

DETAILED DESCRIPTION OF PREFERRED EMBODIMENTS

Certain terminology is used in the following description for convenience only and is not limiting. The words "right," "left," "lower" and "upper" designate directions in the drawings to which reference is made. The words "proximal" and "distal" refer to directions away from and closer to, respectively, for example, the insertion ends of the first and second catheters in a preferred double catheter assembly according to the present invention. The terminology includes the words above specifically mentioned, derivatives thereof, and words of similar import.

Figures 1, 2, 2A, 2B, 3, 4:
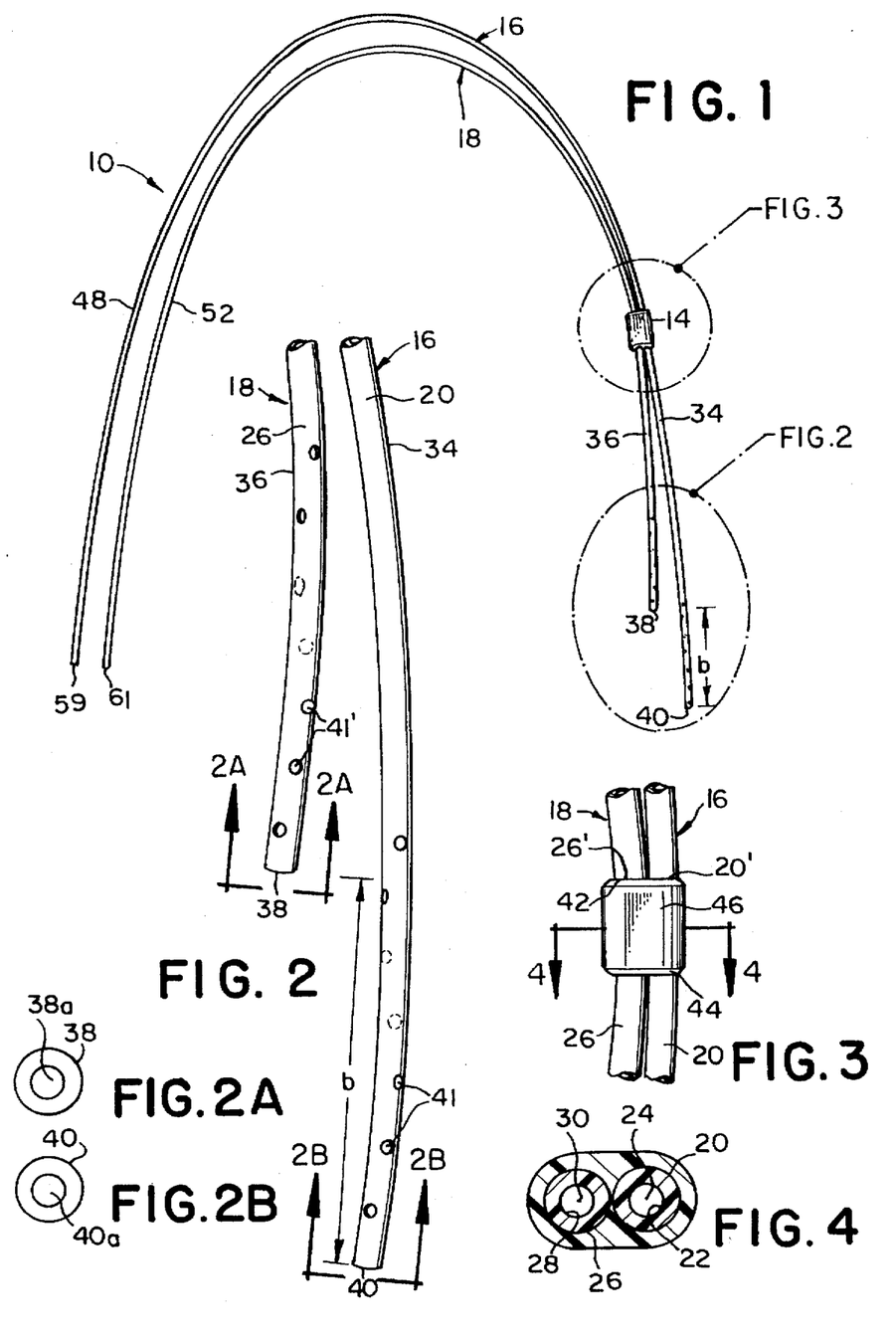
FIG. 1 is a plan view of a preferred embodiment of a self-retaining double catheter assembly according to the present invention.
FIG. 2 is an enlarged plan view of a section of the distal portion of the first and second catheters within the assembly of FIG. 1.
FIG. 2a is a front elevational view of the distal end of one of the catheters in the preferred assembly taken along line 2a—2a of FIG. 2.
FIG. 2b is a front elevational view of the distal end of the other catheter in the preferred assembly taken along line 2b—2b of FIG. 2.
FIG. 3 is an enlarged plan view of the retaining sleeve in the catheter assembly of FIG. 1.
FIG. 4 is an enlarged cross-sectional view of the retaining sleeve shown in FIG. 3 taken along line 4—4.
Figure 5:
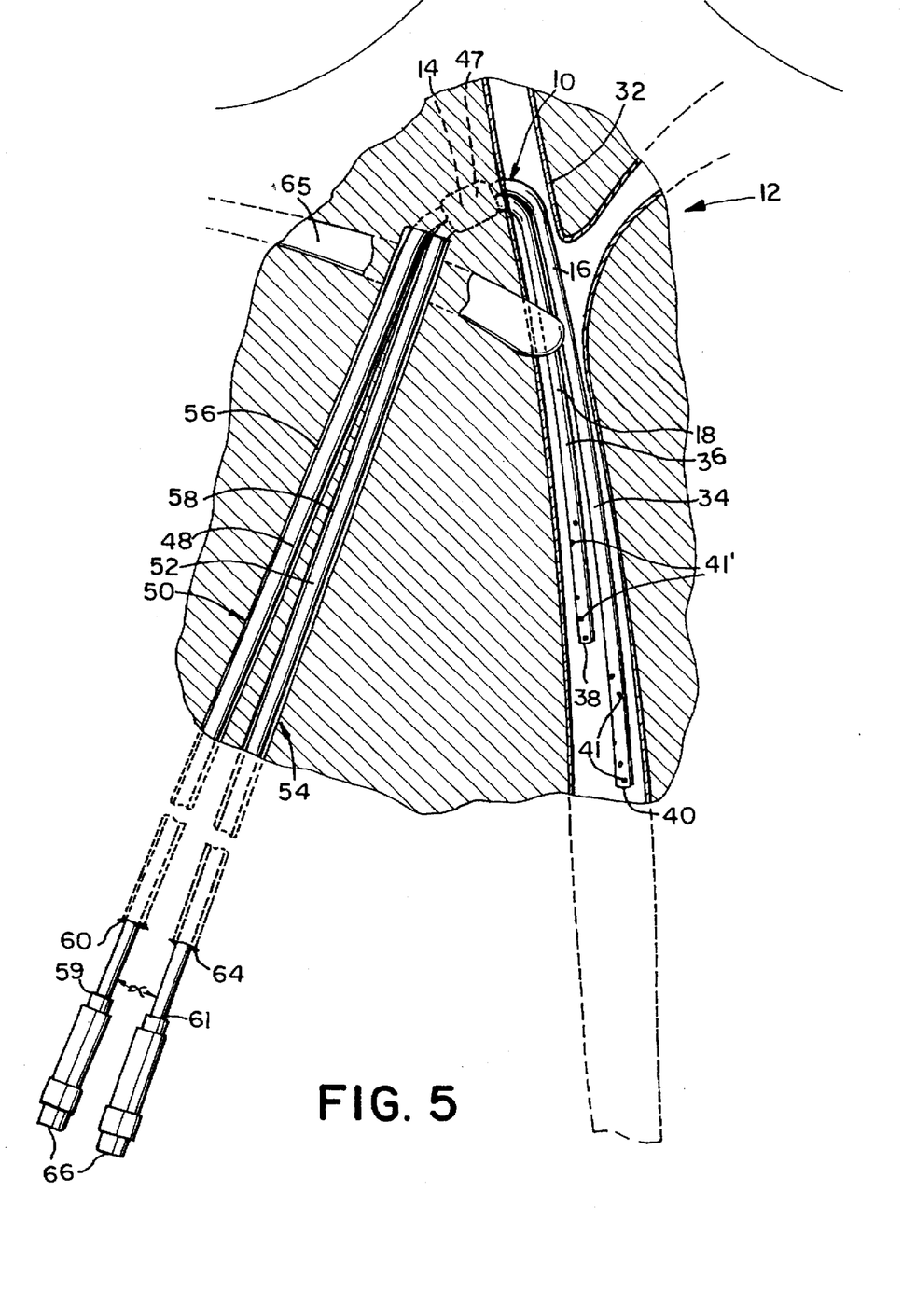
FIG. 5 is partially broken-away diagrammatic view of a preferred embodiment of a catheter assembly according to the present invention secured in position after insertion into a patient's internal jugular vein.

Referring now to the drawings in detail, where like numerals indicate like elements throughout, there are shown in FIGS. 1 through 5, a preferred embodiment of a double catheter assembly, generally indicated as 10. As shown in FIG. 5, once a catheter assembly 10 is properly inserted in an area to be catheterized 12, the assembly 10 is self-retaining in that it is secured by the retaining sleeve generally indicated as 14. As shown in FIG. 1, the assembly 10 according to the present invention includes a first catheter 16, a second catheter 18, and the retaining sleeve 14. It will be understood from the disclosure, that additional catheters (not shown), including multiple lumen catheters, which may have distal portions inserted into the area to be catheterized in a manner as shown in FIG. 5, could also be positioned within the retaining sleeve 14 such that proximal portions of such catheters are drawn out of the body through two or more subcutaneous areas and the retaining sleeve 14 would function to secure all of the catheters in position. Such an assembly is contemplated as within the present invention as an alternative self-retaining assembly adaptable for other related applications. However, for clarity and convenience, the present invention will be described below in the preferred assembly embodiment which includes an improved Tesio system assembly having two single lumen catheters 16, 18 and a retaining sleeve 14 as shown in FIGS. 1–5.

The catheter assembly 10 can be adapted for use in various applications in which bodily fluids, medicaments or other solutions are introduced and removed from the body such as perfusion, infusion, plasmapheresis, hemodialysis, chemotherapy, and the like. For the purposes of describing the preferred embodiment of the present invention, the device will be described with respect to the preferred application of hemodialysis. However, it should be understood by one skilled in the art based on this disclosure, that the assembly 10 can be configured and adapted, by increasing or decreasing the catheter size and/or number and by positioning the retaining sleeve, such that the assembly 10 can be beneficially used for other medical applications in which fluids are introduced and/or removed from the body.

The first catheter 16, the second catheter 18 and the retaining sleeve 14 are all preferably made of a biocompatible plastic or elastomer, more preferably from a biocompatible elastomer. Suitable biocompatible plastics include materials such as, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethylstyrene and other similar compounds known to those skilled in the art. It should be understood that these possible biocompatible polymers are included above for exemplary purposes and should not be construed as limiting. If a biocompatible polymeric material is used to form the catheters 16, 18 and the retaining sleeve 14, it is most preferred that the polymeric material includes a polyurethane or a polyolefin polymeric material.

Suitable, preferred, biocompatible elastomers for use in forming the catheters 16, 18 and the retaining sleeve 14 include biocompatible elastomers such as medical grade silicone rubbers, polyvinyl chloride elastomers, polyolefin homopolymeric and copolymeric elastomers, urethane-based elastomers, and natural rubber or other synthetic rubbers. Preferably, the catheters 16, 18 and the retaining sleeve 14 are made of the elastomeric material such that the catheters 16, 18 and retaining sleeve 14 are flexible, durable, soft, and easily conformable to the shape of the area to be catheterized 12 and/or the subcutaneous areas as described below. It is more preferred that the catheters 16, 18 and retaining sleeve 14, if used for hemodialysis applications particularly, be formed of a silicone elastomer which is preferably capable of withstanding sterilization by autoclave and preferably has a hardness of at least about 80-A on a Shore durometer scale. While it is preferred to have a higher Shore durometer hardness if a biocompatible elastomer is used, particularly for hemodialysis, it is also possible to make a device from an elastomer having a lower Shore durometer hardness without departing from the spirit of the invention. It will be understood, based on this disclosure, that the catheters 16, 18 may also be radiopaque depending on their intended use.

As best shown in FIGS. 2 and 4, the first catheter 16 has an exterior surface 20 and an interior surface 22 defining a first lumen 24. The first lumen 24 extends longitudinally through the first catheter 16, preferably along the full length of the catheter 16. In a similar manner, the second catheter 18 has an exterior surface 26 and an interior surface 28 defining a second lumen 30. The second lumen 30 extends longitudinally through the second catheter 18, preferably along the full length of the catheter 18. The lumens 24, 30 preferably each have a generally circular cross section as viewed along a plane perpendicular to the longitudinal axis of each of the catheters 16, 18. While the circular cross section is preferred in order to achieve efficient fluid flow in each lumen 24, 30, other configurations may be used without departing from the spirit of the present invention, such as for example, oval, elliptical, or kidney-bean shaped. While configurations such as semi-circular, rectangular, and the like may be used, they are not preferred as the sharper corners may increase turbulent flow within the lumens 24, 30. In addition, while two lumens 24, 30 of equal cross-sectional area are preferred, the two lumens 24, 30 in the catheter assembly 10 may be of different cross-sectional areas (such as, for example, providing a smaller lumen for infusion of medication). Alternatively, two lumens 24, 30 of equal cross-sectional area may be provided along with an additional lumen (not shown) which may have the same or a different cross sectional area (such as, for example, a hemodialysis catheter having two lumens of equal cross-sectional area for removal and return of blood and a third lumen of a smaller circular cross-section for infusion of medication).

The catheters 16, 18 can be used for the introduction and removal of fluids from an area to be catheterized, such as the area 12 as shown in FIG. 5. In FIG. 5, the area to be catheterized includes the internal jugular vein 32. Other areas in which the catheter assembly may be used include, for example, other blood vessels, including the femoral and subclavian veins, any abscess cavity, post-operative cavity, the peritoneal cavity, and other areas of the body including intra-abdominal, sub-diaphragmatic and sub-hepatic areas. It should be understood by one of ordinary skill in the art from this disclosure that these areas are exemplary, and that the catheter assembly 10 may be used to remove or introduce fluids in various areas to be catheterized. The preferred embodiment of the invention as shown, is preferably useful for intake, or removal, of blood to be purified from a blood vessel, such as the internal jugular vein 32, and introduction of purified blood into the same vessel as shown in FIG. 5. The blood can be purified by any suitable hemodialysis apparatus (not shown). The catheters 16, 18 may also be used to introduce medication or other fluids such as glucose or saline solutions into the body.

The catheters 16, 18 each include a distal portion 34, 36 respectively as shown in FIGS. 1 and 5. The distal portions 34, 36 are configured to be placed in, or preferably inserted into, the area to be catheterized 12. For example, as shown in FIG. 5, the distal portions 34, 36 of the catheters 16, 18 are configured to have a suitable length and width to be useful for insertion into the internal jugular vein 32. If used for hemodialysis applications particularly, it is preferred that the distal end 38 of the second catheter 18 is proximally and longitudinally spaced from the distal end 40 of the first catheter 16 a sufficient distance b (shown in FIGS. 1 and 5) which substantially prevents recirculation of the purified blood and blood to be purified. The distance b, is preferably about 4 centimeters, however, it should be understood by one of ordinary skill in the art based on this disclosure, that b could be varied for different applications of the catheter assembly 10.

Blood is preferably drawn out of a blood vessel, such as the internal jugular 32 through an opening 40a through the distal end 40 of the first catheter 16 as shown in FIGS. 2b and 5. Preferably the opening 40a through the distal end 40 of the first catheter 16 is coextensive with the first lumen 24. Blood is returned through an opening 38a through the distal end 38 of the second catheter 18 as shown in FIGS. 2a and 5. The opening 38a is preferably coextensive with the second lumen 30.

While it is preferred, if the catheter assembly 10 is used for hemodialysis, that blood be drawn from the distal end 40 of the longer first catheter 16 in the present invention, it should be understood by one of ordinary skill in the art based on this disclosure that the direction of flow can be reversed, in the manner of conventional prior art of multiple lumen catheter designs, such that the distal end 40 of the longer, first catheter 16 is used for returning purified blood, or other fluid, to the area to be catheterized 12, such as the internal jugular vein 32.

The catheter assembly 10 of the present invention, which is preferably used with a flow direction reversed from the conventional flow pattern of prior art catheters in which the longer lumen is the return lumen, provides the benefit of being operational at higher flow rates. In hemodialysis applications, by using the longer lumen 24 of the first catheter 16 in the catheter assembly 10 of the present invention for drawing blood from the area to be catheterized 12, preferably the internal jugular vein 32, the blood to be purified may be safely and efficiently drawn from an area closer to the right atrium of the heart in which the blood has a higher flow rate. As the catheter assembly 10 is designed to function well with high efficiency dialysis devices, it can accommodate high flow rates in the range of 450 cc/min, thereby decreasing the time necessary for a patient to undergo conventional dialysis treatments. The purified blood is returned upstream and proximally from the area where the blood to be purified is drawn a distance of preferably about 4 centimeters. The separation distance b is preferably longer than the traditional spacing of return and intake openings of multiple lumen catheters which is typically about 2 centimeters. The preferred longer distance b, in combination with the ability of the distal portions 34, 36 to move independently in the vessel 32, helps to prevent recirculation of purified blood returned upstream through lumen 30 with blood to be purified being drawn through lumen 24.

The distal ends 40, 38 of the first and second catheters 16, 18, respectively, are preferably blunt in that they are configured to lie generally in a plane which is perpendicular to the longitudinal plane of each catheter 16, 18. The ends may also be slightly rounded (not shown). The ends 40, 38 are preferably integral with the catheters as shown in the preferred embodiment and are preferably formed of a flexible material such as a silicone elastomer as described above. By configuring the distal ends 40, 38 in a blunt design and forming the ends 40, 38 from a material such as a silicone elastomer, trauma to the area to be catheterized 12 and stenosis are minimized. It should be understood from this disclosure that while blunt ends 40, 38 are preferred for hemodialysis applications, other end configurations are possible, such as, for example, tapered or slightly pointed ends which facilitate insertion or accommodate other potential applications of the assembly 10. Such tapered or slightly pointed designs are not preferred for hemodialysis applications of the assembly 10, however, as they tend to increase the risk of vessel wall trauma and stenosis.

As shown in FIG. 2, it is preferred that a first and second plurality of apertures 41, 41' be provided to the distal ends 40, 38 of the first and second catheters 16, 18, respectively. The apertures 41 preferably extend from the exterior surface 20 to the interior surface 22 of the first catheter. The apertures 41' preferably extend from the exterior surface 26 to the interior surface 28 of the second catheter. The apertures 41, 41' preferably provide for more even intake and return flow of fluids through the lumens 30. The apertures 41, 41' also provide alternative openings in the distal portions 34, 36 of the catheters 16, 18 such that flow may continue if the openings 40a, 38a become blocked, clogged or otherwise occluded. By allowing fluid to enter and leave the lumens 24, 30 through the apertures 41, 41', movement of the catheters 16, 18 within the area to be catheterized 12, such as an internal jugular vein 32, which may cause stenosis may be minimized. This phenomenon occurs by providing the apertures 41, 41' in a helical design around the circumference of each of the distal portions 34, 36 of the catheters 16, 18. The helical design, best shown in FIG. 2, helps to equally distribute the flow of fluids entering and leaving the catheters 16, 18 through the alternate flow apertures 41, 41'.

A retaining sleeve 14 is located on the catheter assembly 10 proximal to the distal ends 40, 38 of the first and second catheters 16, 18. The retaining sleeve is positioned around a portion 20' of the exterior surface 20 of the first catheter 16 and a portion 26' of the exterior surface 26 of the second catheter 18. The portions 20', 26' of the exterior surfaces 20, 26 of the first and second catheters 16, 18 within the retaining sleeve 14 are juxtaposed to one another as best shown in FIGS. 3 and 4. While the portions 20', 26' within the sleeve 14 may be spaced from one another, it is preferred that they are close together, preferably touching to avoid entry of bodily fluids such as blood into the retaining sleeve 14. As shown in FIG. 3, the top and bottom edges 42, 44 of the retaining sleeve 14 may be bevelled extending from the external surface 46 of the retaining sleeve 14 toward the exterior surfaces 20, 26 of the catheters 16, 18. Bevelled edges 42, 44 as shown in FIGS. 1 and 3 may help to prevent fluid from entering into the retaining sleeve 14. Alternatively, the edges 42, 44 may be at a substantially right angle to the exterior surface 46 of the retaining sleeve 14. Regardless of the configuration of the edges 42, 44, it is important that the retaining sleeve 14 be made sufficiently wide to prevent the retaining sleeve 14 from passing into the vein 32 or other area to be catheterized 12 such that the retaining sleeve remains outside the area to be catheterized 12 after insertion. As such, the retaining sleeve 14 is preferably sufficiently wide such that is larger than an opening into the area to be catheterized 12 made through the insertion site 47 into the body. In hemodialysis applications, the catheter assembly 10 is preferably introduced by means of a tear-away sheath assembly as described below. Preferably, the retaining sleeve 14 is wider than the tear-away sheath assembly such that it does not pass into the sheath when the distal portions 34, 36 of the catheters 16, 18 are inserted in the vein 32.

The retaining sleeve 14 is preferably positioned in a permanent location along the first and second catheters 16, 18 by either a medical grade adhesive, by heat, or by ultrasonic welding. Any suitable pressure or heat sensitive medical grade adhesive may be used such as, for example, Dow Corning Silicone Medical Grade Adhesive. However, other biocompatible adhesives are also acceptable. Methods for heat-molding or ultrasonically welding the retaining sleeve 14 onto the exterior surfaces 20, 26 of the catheters 16, 18 include any suitable methods which would be known to one of ordinary skill in the art. It should be understood based on this disclosure, that other methods for permanently positioning the retaining sleeve 14 are contemplated.. In addition, while not preferred, the present invention includes a physician, or other medical personnel, positioning the retaining sleeve 14 on the catheters 16, 18 prior to or after insertion of the distal ends 40, 38 of the catheters 16, 18. In the preferred embodiment, however, the retaining sleeve 14 is already permanently positioned on the catheters 16, 18 prior to use to eliminate excess time required for otherwise positioning the sleeve 14 around the catheters 16, 18.

The retaining sleeve 14 is preferably sized to fit snugly around the first and second catheters 16, 18 when the catheters 16, 18 are arranged in a juxtaposed relationship. The retaining sleeve 14, is preferably longitudinally sized to fit within the subcutaneous tissue lying between the entry point to the area to be catheterized, the incision site and any subcutaneous areas for securement. If the catheter assembly 10 is used for hemodialysis and the area to be catheterized 12 is the internal jugular vein 32, an insertion site 47 will be made in the vicinity of the clavicle, as shown, for example in FIG. 5. The exact location of the insertion site 47 can be slightly varied by the physician. The retaining sleeve 14 is sized to fit in a location outside the vein 32, distally beneath the area surrounding the insertion site 47 through the body such that the retaining sleeve 14 may be embedded in subcutaneous tissue as shown, for example, in FIG. 5. The retaining sleeve 14, in hemodialysis applications, is preferably about 1 centimeter in length as measured along a longitudinal axis of the retaining sleeve 14. The inner width of the sleeve 14 is determined in accordance with the outer diameters of the catheters 16, 18 positioned within the sleeve 14 such that a snug fit is preferably provided between the sleeve 14 and the catheters 16, 18. The exterior width of the sleeve 14 is preferably determined such that the sleeve 14 is configured to be sufficiently wide or large such that it does not pass or otherwise enter into the area to be catheterized 12 through an opening into the area to be catheterized 12 made through the insertion site 47 when the catheter assembly 10 is being positioned in the area to be catheterized 12.

The first catheter 16 has a first proximal portion 48 configured to be placed within a first subcutaneous area 50. In a similar manner, the second catheter 18 has a second proximal portion 52 configured to be placed within a second subcutaneous area 54. The first and second subcutaneous areas 50, 54 preferably include first and second subcutaneous tunnels 56, 58, respectively. The subcutaneous tunnels are preferably formed using a tunnelling device (not shown) such as a stainless steel trocar which, for example, attaches to a first proximal end 59 of the first proximal portion 48 of the first catheter 16 and pulls the proximal portion 48 beneath the skin while forming a subcutaneous tunnel 56. The end 59 of the proximal portion 48 is drawn by the device percutaneously out through an opening 60 in the patient's skin preferably about 6 to about 8 inches (about 15.2 to above 20.3 cm) caudal to the insertion site 47 of the catheter assembly 10 such that the first subcutaneous tunnel 56 extends from proximate to the insertion site 47 caudally through the subcutaneous area 50 to the opening 60. The end 59 of the catheter 16, when inserted extends outside the opening 60.

The second proximal end 61 of the second proximal portion 52 of the second catheter 18 is drawn by the device out through an opening 64 in the patient's skin preferably about 6 to 8 inches caudal to the insertion site 47 of the catheter assembly 10 such that the second subcutaneous tunnel 58 extends from proximate to the insertion site 47 caudally through the subcutaneous area 54 to the opening 64. When inserted, the end 61 extends outside the opening 64. The opening 60 and the opening 64 are spaced a distance from one another such that an acute angle α is formed between a line extending from the retaining sleeve 14 to the opening 60 and a line extending from the retaining sleeve 14 to the opening 64. The angle α between the tunnels 56, 58 may be varied from a small angle in which the tunnels 56, 58 are close to parallel to each other to a larger angle in which the tunnels 56, 58 and their openings 60, 64 are further apart without departing from the scope of the invention. It is preferred that the angle α be small enough that flow through the lumens 24, 30 is unobstructed. The angle is preferably from about 5° to about 120°, more preferably from about 5° to about 20°, and most preferably from about 10° to about 15°.

In tunnelling procedures, if the catheter assembly 10 is to be used for hemodialysis and the area to be catheterized 12 is an internal jugular vein 32, it is preferred that the proximal portions 48, 52 are looped over the clavicle 65 as shown in FIG. 5.

While not necessary for retaining purposes, as the device is self-retaining, fabric tissue ingrowth cuffs formed of Dacron® polyester and the like may optionally be provided to the exterior surface 20 of the proximal portions 48, 52 of the catheters 16, 18 if believed to be necessary to prevent infection. It is unknown by applicants, and believed to still be the subject of medical research, whether such cuffs actually help to prevent infection. However, in the event fabric cuffs do help to prevent infection, they may be affixed to the exterior surface 20 of the proximal portions 48, 52. However, such cuffs are not necessary to render the device self-retaining.

Connectors 66 may be attached to the proximal ends 59, 61 of the catheters 16, 18 such that the catheters 16, 18 may be attached to other devices such as, for example, a hemodialysis apparatus or an injection system. Other devices will be apparent to those of ordinary skill in the art based on this disclosure. Examples of suitable connectors 66 include quick connect fittings, ferrule connectors, threadable connectors, and the like. Locks or clamps (not shown), such as, for example, conventional luer locks, may also be provided to the proximal portions 48, 52 of the catheters 16, 18 for regulation or interruption of flow of fluid through the lumens 24, 30.

In placing the catheter assembly 10 in an area to be catheterized 12 such as an internal jugular vein 32 as shown in FIG. 5, a needle (not shown), typically an 18 gauge needle, is used to locate the vein 32 by methods used by those of ordinary skill in the art. A guide wire (not shown) is introduced through the needle into the vein 32. An incision is made at an incision site 47, and a tear-away sheath assembly (preferably about 18 French in diameter) including a sheath and a dilator (not shown) is slipped into the vein 32 over the guide wire in accordance with techniques used by those of ordinary skill in the art. The guide wire and dilator are removed. The catheter assembly 10 is inserted through the sheath (not shown). Alternatively, the sheath may also function as a dilator. The distal portions 34, 36 are introduced into the vein 32 through the sheath until the retaining sleeve 14 is positioned just outside the vein 32. When the retaining sleeve 14 reaches the top of the sheath, the sheath is peeled away leaving the distal portions 34, 36 of the catheters 16, 18 situated in the vein 32.

The proximal portions 48, 52 of the catheters 16, 18 are then tunnelled through the subcutaneous areas 50, 54 as previously described. The incision site 47 and any tunnelling incisions are closed and a dressing is preferably applied. When the proximal portions 48, 52 are positioned in subcutaneous areas 50, 54, preferably in the subcutaneous tunnels 56, 58, the retaining sleeve 14 is embedded in subcutaneous tissue and positioned outside the area to be catheterized 12 and distal to the first and second subcutaneous areas 50, 54. By positioning the retaining sleeve 14 in this manner, a generally Y-shaped configuration is achieved having the angle α as previously described. The retaining sleeve 14 thereby secures the assembly 10 in place, and the assembly 10 cannot be pulled from the area of catheterization 12 or subcutaneous areas 50, 54 due to the location of the retaining sleeve 14 in the subcutaneous tissue between the area to be catheterized 12 and the subcutaneous areas 50, 54. As shown in FIG. 5, the retaining sleeve 14 is positioned outside the vein 32 and distal to the first and second subcutaneous tunnels 56, 58.

Double catheter systems may be improved by providing a retaining sleeve 14 as described above in accordance with the preferred method of the present invention for making a double catheter system self-retaining. Such systems comprise a first and second catheter 16, 18 preferably as described above wherein the distal portions 34, 36 of the catheters 16, 18 are for insertion into an area to be catheterized 12. The catheters 16, 18 also have proximal portions 48, 52, preferably as described above, for insertion into a first and second subcutaneous area 50, 54 respectively. Each of the catheters 16, 18 has a lumen 24, 30 extending longitudinally through its respective catheter 16, 18. The method includes positioning a portion 20' of the exterior surface 20 of the first catheter 16 and a portion 26' of the exterior surface 26 of the second catheter 18 in a juxtaposed relationship within the retaining sleeve 14. Upon insertion of the distal portions 34, 36 of the catheters 16, 18 into the area to be catheterized 12, as described above, the retaining sleeve 14 is outside the area to be catheterized 12 and distal to the first and second subcutaneous areas 50, 54 thereby securing the catheters 16, 18 in the assembly 10. The retaining sleeve 14 may be permanently positioned around the portions 20', 26' of the exterior surfaces 20, 26 of the catheters 16, 18 as described above using either adhesives, heat-molding or ultrasonic welding.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A self-retaining double catheter assembly, comprising:

a first catheter having an exterior surface, an interior surface defining a first lumen extending longitudinally through the first catheter, a proximal portion for placement within a first subcutaneous area, and a distal portion for placement within an area to be catheterized, a distal end of the distal portion of the first catheter having a first opening therethrough;

a second catheter having an exterior surface, an interior surface defining a second lumen extending longitudinally through the second catheter, a proximal portion for placement within a second subcutaneous area, and a distal portion for placement within an area to be catheterized, a distal end of the distal portion of the second catheter having a second opening therethrough; and a retaining sleeve positioned around a portion of the exterior surface of the first catheter located proximal to the distal portion of the first catheter and around a portion of the exterior surface of the second catheter located proximal to the distal portion of the second catheter, wherein the portions of the exterior surfaces of the first and second catheters within the retaining sleeve are in a juxtaposed relationship and the first and second catheters are affixed within the retaining sleeve, the retaining sleeve being positioned such that when the distal portions of the first and second catheters are within an area to be catheterized and the proximal portions of the first and second catheters are within first and second subcutaneous areas, the retaining sleeve is outside the area to be catheterized and distal to first and second subcutaneous areas and the assembly is subcutaneously secured in place by the retaining sleeve.

2. The self-retaining double catheter assembly according to claim 1, wherein the first catheter and the second catheter are flexible.

3. The self-retaining double catheter assembly according to claim 2, wherein the first catheter and the second catheter comprise a silicone elastomer.

4. The self-retaining double catheter assembly according to claim 1, wherein the first catheter has a generally circular cross section taken along a plane perpendicular to the longitudinal axis of the first catheter, and the second catheter has a generally circular cross section taken along a plane perpendicular to a longitudinal axis of the second catheter.

5. The self-retaining double catheter assembly according to claim 1, wherein the retaining sleeve is positioned on and fixed to the first and second catheters for subcutaneously securing the assembly such that when the proximal portions of the first and second catheters are within first and second subcutaneous tunnels respectively and the distal portions of the catheter assembly are within an area to be catheterized, the retaining sleeve is subcutaneously embedded outside the area to be catheterized and distal to the first and second subcutaneous tunnels, and the catheter assembly forms a Y-shaped configuration.

6. The self-retaining double catheter assembly according to claim 1, wherein the retaining sleeve comprises a biocompatible material selected from the group consisting of polyolefin, polyurethane and silicone elastomer.

7. The self-retaining double catheter assembly according to claim 1, wherein the first catheter further comprises a first proximal end and the second catheter further comprises a second proximal end, the first and second proximal ends configured to be drawn percutaneously from the first and second subcutaneous areas outside of a body.

8. The self-retaining double catheter assembly according to claim 7, wherein the assembly further comprises connectors attached to the proximal ends of the first and second catheters, and locks located distal to the connectors for regulating flow through the first and second lumens.

9. The self-retaining double catheter assembly according to claim 1, wherein the distal portion of the first catheter is configured to be placed in a blood vessel for the intake of blood to be purified in a hemodialysis apparatus through the distal opening of the first catheter, and the distal portion of the second catheter is configured to be placed in a blood vessel for the return of purified blood from a hemodialysis apparatus through the distal opening of the second catheter, the distal end of the second catheter being longitudinally spaced a sufficient distance from the distal end of the first catheter to substantially prevent recirculation of purified blood and blood to be purified.

10. The self-retaining double catheter assembly according to claim 9, wherein the distal opening of the second catheter is longitudinally spaced about 4 centimeters from the distal opening of the first catheter.

11. The self-retaining double catheter assembly according to claim 1, wherein a first plurality of apertures is provided to the distal portion of the first catheter, and a second plurality of apertures is provided to the distal portion of the second catheter, the first plurality of apertures extending from the exterior surface to the interior surface of the first catheter and the second plurality of apertures extending from the exterior surface to the interior surface of the second catheter.

12. The self-retaining double catheter assembly according to claim 11, wherein the first plurality of apertures is arranged in a helical configuration around a circumference of the first catheter and the second plurality of apertures is arranged in a helical configuration around a circumference of the second catheter.

13. The self-retaining double catheter assembly according to claim 1, wherein the distal end of the first catheter and the distal end of the second catheter are blunt such that trauma to the area to be catheterized is minimized.

14. The self-retaining double catheter assembly according to claim 1, wherein the retaining sleeve has a length as measured along a longitudinal axis of the sleeve of about 1 centimeter.

15. The self-retaining double catheter assembly according to claim 1, wherein the retaining sleeve is configured to be larger than an opening into the area to be catheterized such that the retaining sleeve remains outside the area to be catheterized.

16. In a double catheter system comprising a first catheter having a first lumen extending longitudinally therethrough, and a second catheter having a second lumen extending longitudinally therethrough, a distal portion of the first catheter and a distal portion of the second catheter being configured to be placed within an area to be catheterized, a proximal portion of the first catheter being configured to be placed within a first subcutaneous area, and a proximal portion of the second catheter being configured to be placed within a second subcutaneous area, the improvement comprising:

a retaining sleeve positioned around and fixed to a portion of the first catheter and a portion of the second catheter such that the portion of the first catheter within the retaining sleeve is juxtaposed to the portion of the second catheter within the sleeve, wherein the retaining sleeve is positioned such that when the distal portions of the first and second catheters are within an area to be catheterized and the proximal portions of the first and second catheters are within first and second subcutaneous areas respectively, the retaining sleeve is located outside the area to be catheterized and distal to the first and second subcutaneous areas and the first and second catheters are subcutaneously secured in place by the retaining sleeve.

17. A method for making a double catheter system self-retaining, wherein the system comprises a first catheter having an exterior surface, a distal portion for insertion into an area to be catheterized, a proximal portion for placement in a first subcutaneous area, and a first lumen extending longitudinally through the first catheter, and a second catheter having an exterior surface, a distal portion for insertion into an area to be catheterized, a proximal portion for placement in a second subcutaneous area, and a second lumen extending longitudinally through the second catheter, the method comprising positioning and fixing a portion of the exterior surface of the first catheter and a portion of the exterior surface of the second catheter in a juxtaposed relationship within a retaining sleeve, wherein upon insertion of the distal portions of the first and second catheters into an area to be catheterized and placement of the proximal portions of the first and second catheters in first and second subcutaneous areas, the retaining sleeve is outside the area to be catheterized and distal to the first and second subcutaneous areas and the first and second catheters are subcutaneously secured in place by the retaining sleeve.

18. The method according to claim 17, wherein the retaining sleeve is permanently positioned around the portions of the exterior surfaces of the first and second catheters by affixing the retaining sleeve to the exterior surfaces of the first and second catheters by use of a biocompatible medical grade adhesive.

19. The method according to claim 17, wherein the retaining sleeve is permanently positioned around the portions of the exterior surfaces of the first and second catheters by at least one of heat-bonding and ultrasonic welding.

* * * * *